(12) United States Patent
Muchnik

(10) Patent No.: US 7,298,469 B2
(45) Date of Patent: Nov. 20, 2007

(54) SPECIFIC DENSITY DETECTOR WITH ELECTRO MECHANICAL ACTUATOR AND IMPROVED MIRROR

(75) Inventor: Boris J. Muchnik, Denver, CO (US)

(73) Assignee: Nuclear Solutions, Inc., Washington, DC (US)

( * ) Notice: Subject to any disclaimer, the term of this patent is extended or adjusted under 35 U.S.C. 154(b) by 189 days.

(21) Appl. No.: 11/048,041

(22) Filed: Jan. 31, 2005

(65) Prior Publication Data
US 2006/0170933 A1    Aug. 3, 2006

Related U.S. Application Data

(63) Continuation-in-part of application No. 10/965,164, filed on Oct. 14, 2004, now abandoned.

(51) Int. Cl.
*G01J 1/00* (2006.01)
(52) U.S. Cl. .................................................. 356/213
(58) Field of Classification Search ..................... None
See application file for complete search history.

(56) References Cited

U.S. PATENT DOCUMENTS

| 4,732,472 A | * | 3/1988 | Konig et al. | 356/152.3 |
| 5,549,114 A | * | 8/1996 | Petersen et al. | 600/504 |
| 5,638,189 A | * | 6/1997 | Yanagisawa | 358/481 |
| 5,877,884 A | * | 3/1999 | Yanagisawa | 359/198 |

* cited by examiner

*Primary Examiner*—Michael P. Stafira
(74) *Attorney, Agent, or Firm*—Michael L. Greenberg, Esq.; Greenberg & Leiberman, LLC

(57) ABSTRACT

An object is placed at a particular distance away from the nonreflecting side of a mirror, such that the gravitational force of the object affects the mirror. A laser is then pointed at the opposite, reflecting side of the mirror, thereby itself reflecting off the mirror and going back in to the cavity of the laser, creating a mode-hopping effect. The mirror will be affected by three forces, the force of a spring ($F_S$), the force of a modulating signal ($F_{MS}$), created by an electro mechanical device attached to the mirror, and the gravitational force of objects as they approach and recede away from the mirror.

3 Claims, 2 Drawing Sheets

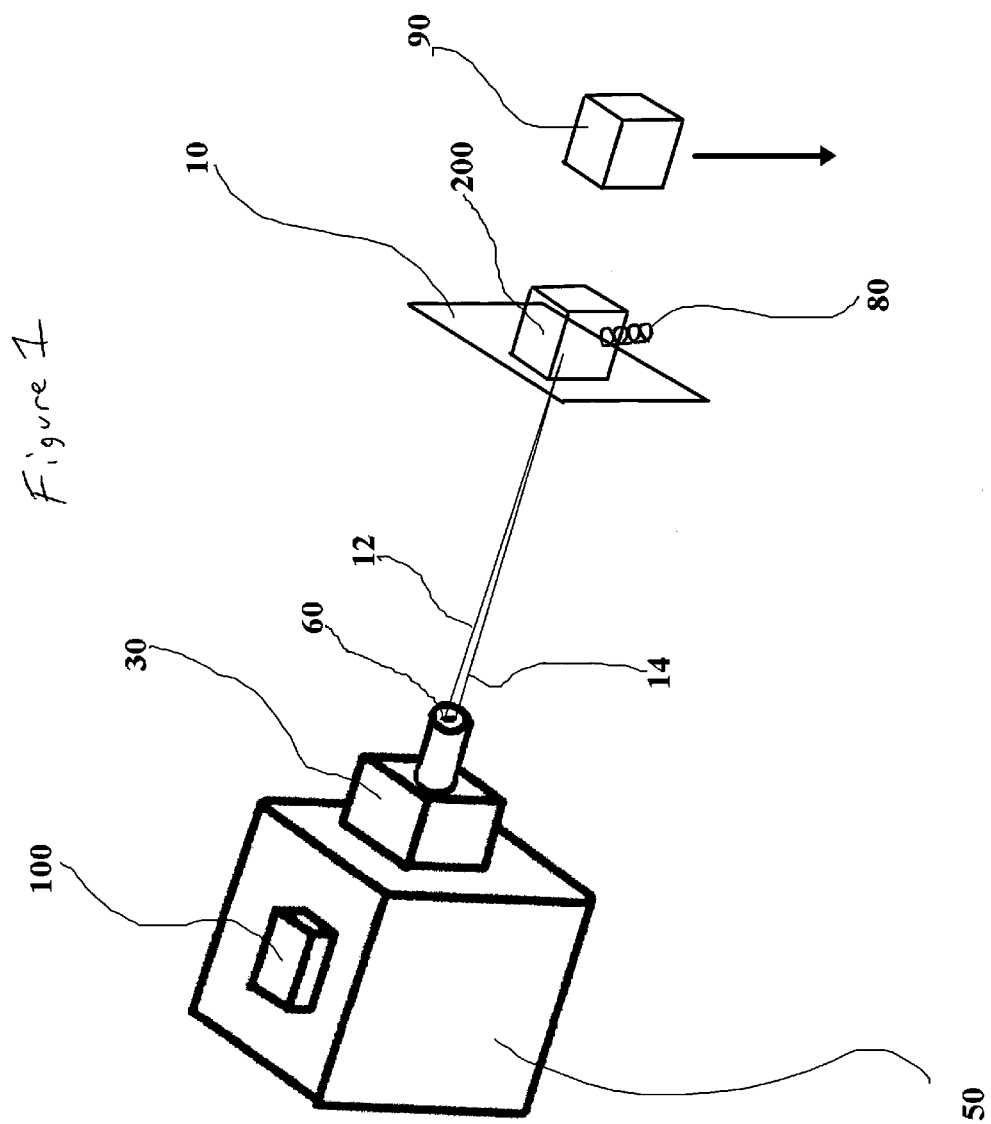

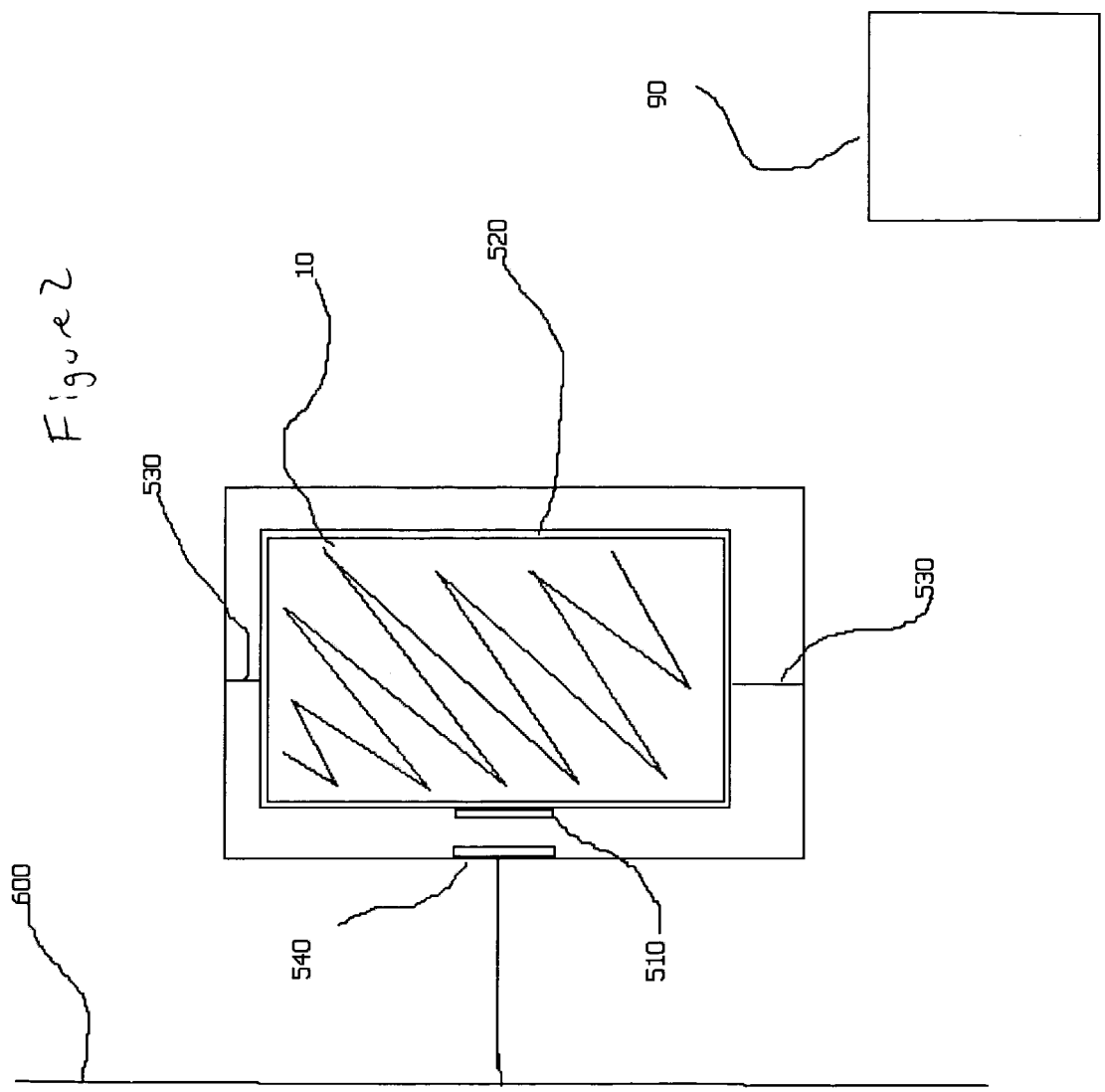

SPECIFIC DENSITY DETECTOR WITH ELECTRO MECHANICAL ACTUATOR AND IMPROVED MIRROR

Priority is hereby claimed to U.S. patent application Ser. No. 10/965,164 filed on Oct. 14, 2004 now abandoned. This is a continuation in part of application Ser. No. 10/965,164.

FIELD OF THE INVENTION

The present invention is a system for detecting the specific density of objects, and more particularly, identifying objects according to their specific density.

BACKGROUND OF THE INVENTION

Detection of objects is important in many applications. For example, for security reasons, detection of objects is important to avoid allowing banned objects from entering and/or exiting a building, plane, or other location. Detection of objects can be difficult, however, if the detection is merely visual, as objects can easily be concealed from view. Thus, entrances to courthouses employ metal detectors to detect any sort of gun, knife of other typically metallic dangerous weapon.

Detection of metallic objects is not adequate for many security applications, as there are many objects that are undesirable that are not metallic whatsoever. And if visual inspection is not adequate to properly detect undesirable objects, then there is a need for a system that can accurately detect objects or else undesirable objects will remain undetected.

Detection of objects is also important for tracking or identification purposes wholly separate from security. It is desirable to correctly identify an object so that its movement can be accurately tracked, even when there is no viable means of placing a tracer, beacon, or other identification marking or code on the object. Thus, there is a need for a system that can detect an object so that the object's movement can be tracked without placing tracking means on the object.

Any object detection system relies on a property or characteristic of an object. For example, if the detection system is visual, the contour or the color of an object might be relied upon to detect certain objects. The specific density is one of many properties of an object, and remains static. Once an object's specific density is known, that object can be detected. However, the problem remains how to detect the specific density of an object if that object is not to be disturbed. Thus, there is a need for system for detecting the specific density of an object so that the object can be identified, wherein the object remains undisturbed.

The present invention deals with two high level concepts that are common in the art. The first concept is mode-hopping. Mode-hopping is an energy transfer from one transverse electronic mode (TEM) to another. For example, the most common mode hopping occurs between the fundamental mode (TEM00) and the donut mode (TEM01). Mode-hopping has been observed in semiconductor lasers due to the laser light fed back in to the laser cavity as a result of reflections. The laser energy distribution in a beam will switch from one mode to another as a function of the laser light fed back in to the cavity.

Inventions that discuss the mode-hopping phenomenon usually discuss the negative aspects. Mode-hopping is seen as a drawback to most lasers, particularly as it deals with an increase in temperature. Mode-hopping creates a situation by which, for a given pumping current, the laser can hop to a completely different mode. This "instability" has been linked to the occurrence of unwanted intensity noise, a change in injection strength (detuning), a reduction in beam power, and overall distress to users of various mechanisms utilizing lasers (including semiconductor lasers in compact disc players and bar-code scanners).

Mode-hopping has also been connected to problems other than use of lasers. In telecommunications, the switching from one mode to another affects the maximum data transmission rate, because different wavelengths have different velocities in single-mode fibers with high dispersion.

The second concept common in the art is the gravity meter, also known as a gradiometer. The concept of gradiometers has been known for some considerable time. Gradiometers measure the differential curvature or ellipticity of gravity equipotential surfaces, the rate of change of the increase of gravity in the horizontal direction, and/or the rate of increase of gravity in the vertical direction. Their object is to measure small changes in the acceleration of a mass due to gravity, known as "g". Through discovery of "g", one can determine the mass, specific density, etc. of a given space.

While gradiometers provide a method by which to obtain data regarding spaces, particularly dealing with land surveillance, most gradiometers have been expensive to manufacture and are unsuitable for long-term installation in the field. Because of the expense, care and accuracy that need to be put into their use, gradiometers are not suitable for everyday use. Furthermore, the gravity gradient measurements are associated with significant noise patterns.

SUMMARY OF THE INVENTION

The present invention introduces mode-hopping as a method by which one can determine the specific density of an object at a distance. An object is placed at a particular distance away from the nonreflecting side of a mirror, such that the gravitational force of the object affects the mirror. A laser is then pointed at the opposite, reflecting side of the mirror, thereby itself reflecting off the mirror and going back in to the cavity of the laser, creating a mode-hopping effect. The mirror will be affected by three forces, the force of a spring ($F_S$), the force of a modulating signal ($F_{MS}$), created by an electro mechanical device attached to the mirror, and the gravitational force of objects as they approach and recede away from the mirror.

Attached to the laser will be a microprocessor that will record the occurring mode-hopping activity. Because the gravitational force imposed on the mirror will change due to the gravitational force of the moving object ($F_{MU}$) as a result of the distance changing between the mirror and the object, it is necessary for either the present invention or the object to move because it is the change in the distance that is being measured—and without the movement the present invention will not function. The present invention will take into consideration $F_S$, $F_{MS}$, $F_{MU}$ and the distance between the object and the mirror, the change in the gravitational force on the mirror is calculated and plotted on a graph. By taking the second derivative of that function, the rate of change of the gravitational force between the mirror and the object is deducted, which is proportional to the specific density of the object.

One use for the present invention, although not solely limited to this use, is for detection of nuclear bombs and other heavy metal objects.

BRIEF DESCRIPTION OF THE DRAWING

FIG. 1 shows an environmental perspective view of the present invention.

FIG. 2 shows an environmental perspective view of the miror.

DETAILED DESCRIPTION OF THE PREFERRED EMBODIMENTS

The present invention contains a (HSL) laser (50), which emits laser beams (12) towards an asymmetrically mounted mirror (amm) (10); the mirror (10) is positioned such that the reflecting side is facing towards the laser (50). The heterostructure laser (50) emits beams (12) that enter a collimating lens (30), which is normally part of the commercially available semiconductor lasers. The collimating lens (30) directs the beams (12) such that they are directed in a straight line towards the mirror (10). The emitted beams (12) then go through a narrow slit (60). The emitted beams (12) then reflect off the mirror (10), reflecting back to the laser (50), and the elements of the return beams (14) which go through the narrow slit (60) will go back in to the cavity of the laser (50), thereby creating a mode-hopping effect and depressing the single mode hopping mode. The system is optically aligned to maximize the effect of suppressing the single fundamental mode. This minimizes the emitted beams (12) of the laser (50). Any misalignment of the mirror (10) will cause the increase in the intensity of the output of the emitted beams (12).

The mirror (10) is mounted as part of the present invention, asymmetrically, via a spring (80) that allows the mirror (10) to move. The return beams (14) are reflected off the mirror (10) in different directions as a result of the movement of the mirror (10). While most of the return beams (14) do not get reflected back into the laser (50), the narrow slit (60) serves to ensure that when return beams (14) are in the correct position, as much light as possible is reflected back into the laser (50) in order to ensure the return beams (14) enter the laser cavity of the laser (50) and mode hopping is maximized.

On the opposite, nonreflecting side of the mirror (10) will be an object (90). The object (90) will have its own gravitational force (FMU). The gravitational force will then be established between the mirror (10) and the object (90). This gravitational force will change as a result of moving the object (90) in the perpendicular direction to the axis of the mirror (10). Due to the change in the distance between the object (90) and the mirror (10), according to Newton's gravitational law the gravitational force is inversely proportional to the square of the distance. This changing force will produce a change in the orientation of the mirror (10), which will subsequently misalign the original optical setup described above. That angle of misalignment, which is proportional to the gravitational force will cause an increase in the return beams (14) and subsequently will become the measure of the gravitational force. The return beams (14) will be then detected and plotted as a function of the changing gravitational force. The second derivative of this plot will be proportional to the specific density of the object (90) and will be deducted electronically by the microprocessor (100) based on the above described measurements. The second derivative of different materials would be associated with specific densities, which will be then calibrated and stored in the microprocessor (100) for comparison to real time objects. Therefore, the microprocessor (100) will be able to distinguish between materials of interest, such as heavy metals or any other object or the lack thereof.

It should be understood that the change in the angle of the mirror and therefore the return beams (14) coming off the mirror (10) is extremely small due to the fact that the gravitational force between the object (90) and the mirror (10) is marginally measurable. Nevertheless, there are numerous methods for amplifying this effect that are commonly known. One of these techniques would be the use of an optical multiplexer (65) commonly used in the telecommunications industry. Optical multiplexers (65) are designed to amplify the input laser beam angle by virtue of multiple internal reflections. Any of the other commonly known methods for such amplification are included in this patent by reference, and are described in more detail below.

The mode-hopping is detected out of laser (50) is the same as that used in a standard cd player. Detection method is that as conventionally known.

The force of gravity is weakest of the fundamental forces, and therefore the angle Theta, of the swing of the laser (50), which is the difference between the angle of the emitted beams (12) and the return beams (14), will necessarily be quite small. Hence, a method to amplify Theta, beyond that which has already been described, is needed. Quite simply, amplification of Theta will ensure that the smallest of swings can be detected.

One method of amplification is to attach an electro mechanical actuator (200) ("EMA") to the mirror (10). The idea behind the EMA (200) is to overlay a regular signal in the 1 to 10 kHz range on the permanent signal created by the gravitational force. This will create an alternating signal in the conventional cavity of laser (50) as a result of the oscillating mirror (10), and allow the change in gravitational force to be more easily measured as the object (90) moves in the perpendicular direction to the axis of the mirror (10). The reason these oscillations make it easier for the gravitational force to be detected is that an oscillating signal is more easily amplified by electronic means.

The preferred EMA (200) would be a conventional piezo electric actuator attached to the mirror (10). The mirror (10) could be physically set and forced in to position with spring (80); however, the preferred method would be to support the mirror (10) with conventional magnetic suspension. The mirror (10) could be set up as follows: A return magnet (540) is used to move the mirror (10) back to its zero position—its position when object (90) is not moving past the mirror (10). Return magnet (540) is positioned adjacent to frame magnet (520), and return magnet (540) is the same polarity as wire magnet (510). Return magnet (540) attracts wire magnet (510) back to the zero position of the mirror (10) once object (90) has passed the mirror (10). The amount of attraction between return magnet (540) and wire magnet (510) can be easily chosen by picking the strength of wire magnet (510) or return magnet (540).

Another physical change to the present invention would allow the change in gravitational force to be more accurately measured as the object (90) moves in the perpendicular direction to the axis of the mirror (10), is to alter the mirror mounting so as to make the movement of the mirror (10) easier and more reliable. The spring (80) is limited to the physical tensile strength of the wire of which it is composed. Over time, due to the constant movement of the spring (10), the tensile strength of the wire changes as the wire is continually bent back and forth. If the spring (80) cannot be relied upon to allow the mirror to move reliably over time, then the present invention might not produce equivalent readings from the same object (90) passing by the mirror (10) in trials performed over time.

By substituting the spring (80) with a conventional magnetic suspension of the mirror (10), the magnetic suspension can be adjusted to allow for extreme fine tuning of the amount of force necessary to move the mirror (10). Magnetic suspension will allow movement of the mirror (10) in response to the object (90) to occur to a greater extent, without resistance from spring (80). In other words, by employing magnetic suspension, if the amount of force necessary to move the mirror (10) is minimal, then not only would the movement of the mirror (10) in response to the object (90) moving in the perpendicular direction to the axis of the mirror (10) be greater than if a spring (80) were employed; but moreover, the movement of the mirror (10) is always constant as magnetic forces will not vary as will the tension of spring (80). Use of magnetic suspension is therefore a superior method for suspension of the mirror (10).

There are numerous methods for creating magnetic suspension for the present invention in place of spring (80). The preferred embodiment of the present invention has a wire magnet (510) wrapped around the periphery of the mirror (10). The wire magnet (510) is wrapped around the periphery of mirror (10) so as to not interfere with the path of laser (50). The wire magnet (510) is of one polarity, while a frame magnet (520) is of an opposite polarity. The frame magnet (520) is essentially a conventional magnetic frame positioned around, but not in physical communication with, the mirror (10). Because of the magnetic repulsion between frame magnet (520) and wire magnet (510), the mirror (10) is held in position without great physical restraints. Dual non-magnetic pins (530) emanate from the top and the bottom of the frame magnet (520), and protrude into the mirror (10) to prevent mirror (10) from falling from frame magnet (520). As the object (90) moves in the perpendicular direction to the axis of the mirror (10), the mirror (10) moves in response to the gravity of object (90), and at the same time, moves ever so slightly about pins (530). A conventional stand (600) is provided to hold The present invention is not limited to the embodiments described above, but also has all embodiments within the scope of the following claims.

I claim:

1. A method for detecting specific density, comprising:
    firing a first laser beam at a front side of a mirror, said first laser beam fired from a cavity;
    passing an object past a backside of said mirror;
    measuring mode hopping in said cavity;
    plotting a second laser beam, said second laser beam being said first laser beam reflected from said mirror, as a function of the changing gravitational force of said object;
    determining a second derivative from plotting said laser beam as a function of the changing gravitational force of said object;
    determining a specific density of said object in proportion to said second derivative;
    mounting said mirror in a flexible fashion so that said mirror moves in response to passing the object past the backside of said mirror;
    mounting an electro mechanical actuator to said mirror as an amplifier by overlaying a regular signal in the 1 to 10 khz range on the permanent signal created by the gravitational force; and
    identifying said object based on the specific density of said object.

2. A method for detecting specific density, comprising:
    firing a first laser beam at a front side of a mirror, said first laser beam fired from a cavity;
    passing an object past a backside of said mirror;
    measuring mode hopping in said cavity;
    plotting a second laser beam, said second laser beam being said first laser beam reflected from said mirror, as a function of the changing gravitational force of said object;
    determining a second derivative from plotting said laser beam as a function of the changing gravitational force of said object;
    determining a specific density of said object in proportion to said second derivative;
    identifying said object based on the specific density of said object; and
    wherein the flexibility of said mirror is achieved by a conventional magnetic suspension.

3. The method of claim 1, wherein said magnetic suspension further comprises a return magnet that will return said mirror into the original position of said mirror.

* * * * *